United States Patent
Goto et al.

(10) Patent No.: US 6,815,417 B1
(45) Date of Patent: Nov. 9, 2004

(54) METHOD FOR TREATING OBESITY AND FOR INHIBITING ADIPOCYTE ACTIVITY

(75) Inventors: Masaaki Goto, Tochigi (JP); Akihiro Tomoyasu, Tochigi (JP); Kyoji Yamaguchi, Omiya (JP); Masahiko Kinosaki, Tochigi (JP); Nobuaki Nakagawa, Tochigi (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/787,397

(22) PCT Filed: Sep. 17, 1999

(86) PCT No.: PCT/JP99/05080

§ 371 (c)(1),
(2), (4) Date: May 17, 2001

(87) PCT Pub. No.: WO00/16795

PCT Pub. Date: Mar. 30, 2000

(30) Foreign Application Priority Data

Sep. 17, 1998 (JP) .......................................... 10-263004

(51) Int. Cl.[7] .......................... A61K 38/17; C07K 14/47
(52) U.S. Cl. .............................. 514/12; 514/2; 514/909; 530/350; 530/399
(58) Field of Search .............................. 514/2, 12, 909; 530/300, 399, 350

(56) References Cited

U.S. PATENT DOCUMENTS 5,837,498 A  11/1998  Olsen et al.
5,877,290 A   3/1999  Olsen et al.

FOREIGN PATENT DOCUMENTS

WO        WO 95/24411        9/1995

OTHER PUBLICATIONS

Rink. Nature. 372: 406–407, Dec. 1994.*
Korner et al. N. Engl. J. Med. 349(10): 926–928, 2003.*
Science, 280: 1363–1387, 1998.*
Lea–Currie et al., Dehydroepiandrosterone Reduces Proliferation and Differentiation of 3T3–L1 Preadipocytes, Biochemical and Biophysical Research Communications 248, 1998, 497–504.

* cited by examiner

Primary Examiner—Christine J. Saoud
(74) Attorney, Agent, or Firm—Hollander Law Firm, P.L.C.

(57) ABSTRACT

A method for treating obesity includes administering to humans or animals a pharmaceutically effective amount of stanniocalcin in the form of a pharmaceutical composition. Stanniocalcin has an excellent activity of inhibiting the differentiation and maturation of adipocytes and therefore is useful as a drug for treating obesity.

14 Claims, No Drawings

METHOD FOR TREATING OBESITY AND FOR INHIBITING ADIPOCYTE ACTIVITY

This application is a 371 U.S. national stage application of international application PCT/JP99/05080 filed Sep. 17, 1999, which claims priority of Japanese patent application 10-263004 filed Sep. 17, 1998.

TECHNICAL FIELD

The present invention relates to a novel preventive and/or therapeutic for obesity.

A pharmaceutical preparation of the present invention has excellent preventive and/or therapeutic effects for obesity and is useful as a pharmaceutical.

BACKGROUND ART

Obesity is a risk factor of diseases such as diabetes mellitus, hypertonia, and heart disease, which threaten health of people in advanced countries. Obesity means physical conditions wherein adipose tissues have abnormally accumulated. Adipose tissues are special organs wherein surplus in vivo energies are stored as fat or triglyceride, and constructed of fibroblasts including adipocytes and their precursors, macrophages, blood vessel surrounding cells, blood cells, and the like.

Adipocytes are said to amount from ⅓ to ⅔ of cells which are present in adipose tissues and to accumulate fats or triglycerides therein. Adipocytes differentiate and mature through the process starting from mesenchymal multipotent stem cells, and growing into lipoblasts which have acquired a base as adipocytes, precursor adipocytes with no lipid droplets but having initial markers of adipocytes, immatured adipocytes containing lipid droplets, and finally into matured adipocytes containing a large quantity of accumulated fats. Adipocytes of adults suffering from slight obesity hypertrophically grow due to increase in the amount of accumulated triglyceride. Number of adipocytes increases as the degree of obesity becomes conspicuous. Therefore, decreasing the number of adipocytes by controlling differentiation and maturation or suppressing hypertrophia of matured adipocytes are expected to stop progress of obesity by suppressing the increase in the amount of accumulated fats, and to treat obesity. Control of in vivo adipocyte differentiation has been proven to undergo either positively or negatively according to a number of factors derived from environmental factors such as ingestion, exercise, and so on. As cytokines which control differentiation of adipocytes from adipocyte precursors, tumor necrosis factor-α (TNF-α: Torti F. M. et al., Science, Vol. 229, p 867 (1985)), transforming growth factor-β (Ignotz R. A. et al., Proc. Natl. Acad. Sci. USA, Vol. 82, p 8530 (1985)), preadipocyte factor-1 (Pref-1: Smas C. M. et al., Cell, Vol. 73, p 725 (1993)), and the like have been reported. In addition, leptin, the translational product of an ob gene which has recently been cloned, has been reported to possibly decrease the intake amount and the weight of adipose tissues via central nerve system (Levin N. et al. Proc. Natl. Acad. Sci. USA, Vol. 93. P 1726, 1996).

Furthermore, intracerebral peptide-neuropeptide Y which exhibits a strong appetite stimulating effect and its receptor are gathering attention as materials for the development of an obesity suppressing pharmaceutical (Sainsburg A. et al, Diabetologia, Vol. 39, p353, 1996). These cytokines are expected to become a therapeutic agent for obesity due to their adipocyte depressing action on accumlation of fat. Clinical tests as an obesity therapeutic or preventive agent is ongoing on some of these cytokines such as leptin.

At present, one obesity therapeutic or preventive agent is commercially available in the USA under the Redux™ (American Home Products Co.). Other drugs such as Meridia (Kunol Co.) and Xenical (Roche Co.) will be approved as an obesity treating agent or a fat absorption inhibitor in the USA. The treatments method using these pharmaceuticals, however, are not necessarily satisfactory in the effects and therapeutic results. Development of a new agent which is available exhibits for these pharmaceuticals higher curative effect and less side effect usable have been desired.

DISCLOSURE OF THE INVENTION

In view of the above circumstances, the present inventors have intensive investigated a substance which shows anti-obesity activity or obesity-curing activity, and as a result, found that stanniocalcin (STC: Olsen H. S. et al., Proc. Natl. Acad. Sci. USA, vol. 93, p 1792 (1996)) which is known as a protein controlling methabolism of minerals, exhibits adipogenesis inhibitory activity, or inhibitory activity of differentiation and/or maturation of adipocytes, which physiologic activity has not been expected of stanniocalcin at all in the past. Accordingly, the object of the present invention is to provide a preventive and/or therapeutical agent for obesity containing a novel substance as an effective ingredient. The present invention relates to a preventive and/or therapeutical agent for obesity, which contains stanniocalcin as an effective ingredient. The pharmaceutical preparation according to the present invention can exhibit excellent preventive and/or therapeutic agent effects for obesity and are useful as a pharmaceutical.

Stanniocalcin was discovered in fishes at first and was subsequently clarified to exist in mammals including humans. Then, cDNA of human embryo was isolated by the genetic engineering procedure on the basis of structural similarity. Human stanniocalcin can be obtained by expressing the resultant cDNA in a variety of cells using the genetic engineering technique.

It has been well known that stanniocalcin reduces a calcium level in vivo when given to fish, and also inhibits phosphate excretion to urine when administered to rats (Proc. Natl. Aca. Sci. USA., 93, 1792 (1996)). However, stanniocalcin has not been known to possess excellent preventive and therapeutic effects for obesity.

THE BEST MODE FOR CARRYING OUT THE INVENTION

Stanniocalcin, or the effective ingredient according to the present invention, can be obtained by the method of Olsen H. S. et al. (Proc. Natl. Acad. Sci. USA, vol. 93, p 1792 (1996)). Specifically, the above-described literature reference or gene bank or the like can besearched to learn the sequence of cDNA of stanniocalcin, and based on the sequence information, stanniocalcin cDNA can be obtained using the PCR method etc. The stanniocalcin expression cell can be obtained by transfections of the expression vector into animal cells etc., the said expression vector is obtained by insertion of the resultant cDNA. Then, stanniocalcin can be obtained by cultivating the resultant stanniocalcin expression cells, followed by purification of the resultant culture solution by conventionally employed procedures. The adipogenesis inhibitory activity can be determined by estimating the suppression effects of adipogenesis induced by dexamethasone with retardation of triglyceride accumulation using mouse preadipocytic cell as a target according to the method of Kodama H. et al. (Journal of Cellular Physiology, Vol. 112, p83 (1982)).

Stanniocalcin, or the effective ingredient of the present invention, can be safely administered to human being and animals in the form of pharmaceutical compositions intended for use in the prevention and/or treatment of obesity. Stanniocalcin can be made into pharmaceutical preparations and administered either for orally or parenterally. Examples of the pharmaceutical composition include compositions for injection, compositions for dripping, suppositories, nasal agent, sublingual agent, percutaneous absorption agent, and the like. These pharmaceutical preparations are formulated according to known pharmaceutical preparation methods using pharmaceutically acceptable carriers, excipients, stabilizers, coloring matters, surfactants and other additives, and made into target preparations. In the case of compositions for injection, a pharmacologically effective amount of stanniocalcin, which is the effective ingredient of the present invention, may be mixed with pharmaceutically acceptable excipients/activators, such as amino acids, sugars, cellulose derivatives and other organic/inorganic compounds, which may be generally added to compositions for injection. If necessary, pH adjusting agents, buffer agents, stabilizers, solubilizing agents, etc. may be added to thereby make a variety of injectable solutions in accordance with the conventional procedures.

Administration thereof is normally done to human adults at a daily dose of 10 µg to 10 mg/kg body weight, as divided in several times, either orally or parenterally. The particularly preferred dosage form is intravenous administration.

EXAMPLE

Examples given in the below describe the present invention in more detail, whereby these examples are merely illustrative, and the present invention is in no way understood to be limited by them.

Example 1

Production of Stanniocalcin i) Isolation of Poly(A)+ RNA From IMR-90 Cells (Pulmonary Fibroblasts of Human Embryo, ATCC CCL-186)

About 10 µg of poly(A)+ RNA was isolated from $1 \times 10^8$ of IMR-90 cells using Fast Track mRNA Isolation Kit (Invitrogen Inc.) according to the protocol of Invitrogen Inc.

ii) Construction of Human Stanniocalcin Expression Vector

A single-stranded cDNA was synthesized using SuperScript II cDNA synthesis Kit (Gibco BRL Inc.) and 1 µg of the isolated poly(A)+ RNA used as a template, according to the protocol of Gibco BRL Inc., Stanniocalcin (STC) cDNA fragment was obtained by carrying out PCR using the obtained cDNA template and primer STCF1N (Sequence Identification No. 1) and primer STCR1Xh (Sequence Identification No. 2) as designed according to the nucleotide sequence of human stanniocalcin. The composition for PCR solution is as follows:

| | |
|---|---|
| 10X Ex Taq Buffer (Takara Shuzo Co.) | 10 µl |
| 2.5 mM dNTP | 8 µl |
| cDNA solution | 1 µl |
| Ex Taq (Takara Shuzo Co.) | 0.5 µl |
| Distilled water | 74.5 µl |
| 20 µM Primer STCF1N | 5 µl |
| 100 µM Primer STCR1Xh | 1 µl |

The above-described solutions were mixed in a microcentrifugal tube, and PCR was performed under the following conditions: after pretreatment at 95° C. for 3 min, the reaction of the three steps of at 95° C. for 30 sec, at 55° C. for 30 sec and at 72° C. for 2 min was repeated 30 times. Then, the reaction mixture incubated at 70° C. for 5 min. A portion of the reaction mixture was subjected to agarose gel electrophoresis, and a uniform DNA fragment of about 900 bp was identified. The fragment was sequenced by the conventional method, and it was confirmed to obtain the cDNA encoding stanniocalcin gene. The cDNA sequence and the amino acid sequence are shown in Sequence Identification Nos. 3 and 4, of sequence table respectively.

The resultant DNA fragment of about 900 bp was purified using QIAEXII DNA extraction kit (QIAGEN Inc.), and the purified DNA was cleaved by restriction enzymes XhoI and NheI (Takara Shuzo Co.) and purified using QIAEXII DNA extraction kit (STC XhoI-NheI fragment). Plasmid pCEP-STC which contained DNA encoding stanniocalcin gene was obtained by ligating the STC XhoI-NheI fragment to pCEP4 (Invitrogen Inc.) cleaved by restriction enzymes XhoI and NheI by ligation kit ver. 2 (Takara Shuzo Co.). E. coli (DH5 α; Gibco BRL Inc.) containing the plasmid has been deposited, in the name of DH5α/pCEP-STC and under Accession No. FERM BP-6736 in National Institute of Bioscience and Human-Technology, Agency of Industrial Science and Technology, The Ministry of International Trade and Industry, located at 1-3, Higashi 1-chome, Tsukuba-shi, Ibaraki-ken, Japan (postal code 305-8566) on May 31, 1999. No erroneous uptake of bases in the DNA portion derived from PCR during the DNA synthesis was meanwhile confirmed by DNA sequencing.

iii) Expression of Human Stanniocalcin

E. coli DH5α having pCEPSTC as obtained in Example 1-ii) was cultivated with shaking in 2 ml of Teriffic Broth (Life Technologies Inc.) containing 50 µg/ml of ampicillin (Sigma Inc.) and 4.7% of glycerol overnight at 37° C., and the plasmid DNA was purified from the bacterial cells using QIAWELL kit (QIAGEN Inc.). 293-EBNA cells (Invitrogen Inc.) in IMDM (Life Technologies Inc.) containing 10% of fetal bovine serum were seeded in each well of a 24-well plate to $2 \times 10^5$/well/ml, followed by cultivation in a $CO_2$ incubator (5% $CO_2$) at 37° C. overnight. PCEPSTC or pCEP4 was transfected to 293-EBNA cells using Fugene 6 (Behringer Mannheim Co.). DNA and Fugene 6 were used in portions of 0.5 µg and 1 µl, respectively. After transfection, the transfected cells were cultivated in a $CO_2$ incubator (5% $CO_2$) at 37° C. for 3 days. The resultant culture solution was assayed for adipogenesis inhibitory activity by the below-described procedure.

iv) Determination of Adipogenesis Inhibitory Activity

Adipogenesis inhibitory activity was determined by the following procedure according to the method of Kodama H. et al. (Journal of Cellular Physiology, Vol. 112, p 83 (1982)): that is, using mouse pre-adipocytic cell strain MC3T3-G2/PA6 (RIKEN GENE BANK, RCB1127) as a target cell, the adipogenesis induced by dexamethasone was determined with triglyceride accumulation as an index of its inhibitory activity. The culture solution from the sample (Example 1-iii)) diluted with α-MEM (Gibco BRL Inc.) containing 10% of fetal bovine serum, the culture solution of cells having the vector alone transfected, and the culture solution of pure 293-EBNA cells were distributed in each portion of 50 µl into 96-well microplate, respectively, and $3 \times 10^3$ cells of pre-adipocytic cell strain MC3T3-G2/PA6 after being suspended in 50 µl of α-MEM containing $2 \times 10^{-7}$ M of dexamethasone and 10% of fetal bovine serum were seeded, followed cultivation at 5% $CO_2$, 37° C. and 100% humidity for one week. After cultivation for 7 days, the culture medium was removed by aspiration, then air-dried and assayed for the triglyceride accumulated in adipocytes with use of a triglyceride measuring kit (Triglyceride G-Test Wako, Code No. 274-69802, Wako Pure Chemicals Ind. Co.). The decreases at OD 510 nm were used for assessment of adipogenesis inhibitory activity. The obtained results are shown in Table 1. As the result, stanniocalcin in the resultant culture solution was confirmed to exhibit adipogenesis inhibitory activity.

TABLE 1

| Dilution | 1/4 | 1/8 | 1/16 | 1/32 |
|---|---|---|---|---|
| Culture solution of STC gene-transfected cells | 0.061 | 0.060 | 0.057 | 0.054 |
| Culture solution of vector-transfected cells | 0.036 | 0.021 | 0.009 | 0.007 |
| Culture solution of 293-EBNA cells | 0.032 | 0.017 | 0.014 | 0.011 |

Example 2

Determination of Adipogenesis Inhibitory Activity Using Cells of Mouse Preadipocytic Cell Strain 3T3/L1

Using mouse pre-adipocytic cell strain 3T3-L1 (deposited at ATCC-Accession No. CL173) as a target, the formation of adipocytes induced by dexamethasone and 1-methyl-3-isobutylxanthine was measured by means of triglyceride accumulation, to determine the suppressing activity against adipocyte formation. Specifically, 50 μl of a sample equivalent to the one in Example 1 diluted with α-MEM (Gibco BRL Inc.) containing 10% of fetal bovine serum was placed into a 96-well microplate, and $5 \times 10^3$ cells of mouse pre-adipocyte 3T3-LI were suspended in 50 μl of α-MEM containing $4 \times 10^{-7}$ of dexamethasone, $2 \times 10^{-5}$ M of 1-methyl-3-isobutylxanthine and 10% of fetal bovine serum and then seeded, followed by cultivation at 5% $CO_2$, 37° C. and 100% humidity for one week. After cultivation for 7 days, the culture medium was removed by aspiration, and the cells were air-dried to measure the triglyceride accumulated in adipocytes using a triglyceride assay kit (Triglyceride G-Test Wako, Code No. 274-69802, Wako Pure Chemicals Ind. Co.). The decrease of OD at 510 nm was taken as adipogenesis inhibitory activity. The obtained results are shown in Table 2. As a result stanniocalcin in the culture solution was confirmed to exhibit adipogenesis inhibitory activity, as in Example 1, when 3T3-L1 cells are used as a target.

TABLE 2

| Dilution | 1/4 | 1/8 | 1/16 | 1/32 |
|---|---|---|---|---|
| Culture solution of STC gene-transfected cells | 0.081 | 0.083 | 0.082 | 0.083 |
| Culture solution of vector-transfected cells | 0.026 | 0.017 | 0.012 | 0.011 |
| Culture solution of 293-EBNA cells | 0.021 | 0.004 | 0.006 | 0.016 |

Example 3

Pharmaceutical Preparation Examples

Pharmaceutical Preparation Example 1

Production of Injection Preparation

One mg of stanniocalcin obtained in Example 1 and 50 mg of human serum albumin were dissolved in 100 ml of 0.01 M phosphate buffer solution (PBS, pH 7.0), and the solution was sterilized, divided into vials (2 ml each), lyophillized and sealed.

Pharmaceutical Preparation Example 2

Production of Injection Preparation

Fifty mg of stannibcalcin obtained in Example 1, 1 mg of Tween 80 and 50 mg of human serum albumin were dissolved in 100 ml of 0.01 M phosphate buffer solution (PBS, pH 7.0), and the solution was sterilized, divided into vials (2 ml each), lyophillized and sealed.

Pharmaceutical Preparation Example 3

Production of Injection Preparation

One hundred mg of stanniocalcin obtained in Example 1, 50 mg of human serum albumin and 4 g of sorbitol were dissolved in 20 ml of 0.01M phosphate buffer solution (PBS, pH 7.0), and the solutionwas sterilized, divided into vials, lyophillized and sealed.

INDUSTRIAL APPLICABILITY

According to the present invention, there is provided a novel preventive and/or therapeutic for obesity, which contains stanniocalcin as an effective ingredient. The pharmaceutical preparation of the present invention can exhibit excellent preventive and/or therapeutic effects against obesity and is useful as a pharmaceutical.

Reference to the Deposited Microorganisms a. Name and address of the Depositary organization in which the relevant microorganisms were deposited:
   Name: National Institute of Bioscience and Human-Technology, Agency of Industrial Science and Technology, The Ministry of International Trade and Industry
   Address: 1–3 Higashi 1-chome, Tsukuba-shi, Ibaraki-ken, Japan (postal code 305-8566)
b. The date when deposit was made with the organization of a. May 31, 1999 (as transferred from Bikoken No. P-16933, which was deposited on Aug. 11, 1998).
c. Accession Number attached to the deposit by the organization of a.
   FERM BP-6736.

What is claimed is:

1. A method for inhibiting adipocyte activity which comprises administering to a human in need of adipocyte inhibiting activity a pharmaceutically effective amount of stanniocalcin in the form of a pharmaceutical composition.

2. A method according to claim 1 wherein said pharmaceutical composition is administered orally or parenterally.

3. A method according to claim 1 wherein said pharmaceutical composition is in a form selected from the group consisting of compositions for injection, compositions for dripping, suppositories, nasal agents, subi ingual agents and percutaneous absorption agents.

4. A method according to claim 1 wherein said pharmaceutical composition further comprises pharmaceutically acceptable carriers, excipients, stabilizers, coloring matters, or surfactants.

5. A method according to claim 1 wherein said pharmaceutical composition is a composition formulated for injection comprising a pharmacologically effective amount of stanoiocalcin and at least one pharmaceutically acceptable excipient and/or activator.

6. A method according to claim 5 wherein said excipient and/or activator comprise amino acids, human serum albumin, sugars, and/or cellulose derivatives.

7. A method according to claim 1 wherein said pharmaceutical composition is administered at a daily dose of 10 μg to 10 mg/kg body weight.

8. A method according to claim 1 wherein said pharmaceutical composition is administered intravenously.

9. A method for inhibiting adipocyte activity according to claim 1, wherein adipocyte differentiation is inhibited.

10. A method for inhibiting adipocyte activity according to claim 1, wherein adipocyte maturation is inhibited.

11. A method for inhibiting adipocyte activily which comprises administering to an animal in need of adipoctye inhibiting activity a pharmaceutically effective amount of stanniocalcin in the form of a pharmaceutical composition.

12. A method for inhibiting adipocyte activity according to claim 11, wherein adipocyte differentiation is inhibited.

13. A method for inhibiting adipocyte activity according to claim 11, wherein adipocyte maturation is inhibited.

14. A method for inhibiting adipogenesis in adipocytes comprising administering a pharmaceutically effective amount of stanniocalcin in the form of a pharmaceutical composition.

* * * * *

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:
      Synthesized DNA

<400> SEQUENCE: 1
ggggctagcc aacaacttag cggaaactt                              29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:
      Synthesized DNA

<400> SEQUENCE: 2
cccctcgagt gtgtcaacac ccctaaaat                              29

<210> SEQ ID NO 3
<211> LENGTH: 741
<212> TYPE: DNA
<213> ORGANISM: Human
<220> FEATURE:
<221> NAME/KEY: promoter
<222> LOCATION: (1)..(3)
<220> FEATURE:
<221> NAME/KEY: terminator
<222> LOCATION: (739)..(741)
<300> PUBLICATION INFORMATION:
<301> AUTHORS: Olsen H. S. et al.
<302> TITLE: Human stanniocalcin: A possible hormonal regulator of
      mineral metabolism.
<303> JOURNAL: Proc. Natl. Acad. Sci. USA
<304> VOLUME: 93
<305> ISSUE: 5
<306> PAGES: 1792
<307> DATE: 1996-03-05
<308> DATABASE ACCESSION NUMBER: GenBank, U46768
<309> DATABASE ENTRY DATE: 1996-02-22

<400> SEQUENCE: 3
atgctccaaa actcagcagt gcttctggtg ctggtgatca gtgcttctgc aacccatgag    60
gcggagcaga atgactctgt gagccccagg aaatcccgag tggcggccca aaactcagct   120
gaagtggttc gttgcctcaa cagtgctcta caggtcggct gcggggcttt tgcatgcctg   180
gaaaactcca cctgtgacac agatgggatg tatgacatct gtaaatcctt cttgtacagc   240
gctgctaaat ttgacactca gggaaaagca ttcgtcaaag agagcttaaa atgcatcgcc   300 aacgggtca cctccaaggt cttcctcgcc attcggaggt gctccacttt ccaaaggatg   360
attgctgagg tgcaggaaga gtgctacagc aagctgaatg tgtgcagcat cgccaagcgg   420
aaccctgaag ccatcactga ggtcgtccag ctgcccaatc acttctccaa cagatactat   480
aacagacttg tccgaagcct gctggaatgt gatgaagaca cagtcagcac aatcagagac   540
agcctgatgg agaaaattgg gcctaacatg gccagcctct tccacatcct gcagacagac   600
cactgtgccc aaacacaccc acgagctgac ttcaacagga gacgcaccaa tgagccgcag   660
aagctgaaag tcctcctcag gaacctccga ggtgaggagg actctccctc ccacatcaaa   720

```
cgcacatccc atgagagtgc a                                                741
```

<210> SEQ ID NO 4
<211> LENGTH: 247
<212> TYPE: PRT
<213> ORGANISM: Human
<300> PUBLICATION INFORMATION:
<301> AUTHORS: Olsen H. S. et al.
<302> TITLE: Human stanniocalcin: A possible hormonal regulator of
       mineral metabolism.
<303> JOURNAL: Proc. Natl. Acad. Sci. USA
<304> VOLUME: 93
<305> ISSUE: 5
<306> PAGES: 1792
<307> DATE: 1996-03-05

<400> SEQUENCE: 4

```
Met Leu Gln Asn Ser Ala Val Leu Leu Val Leu Val Ile Ser Ala Ser
1               5                   10                  15

Ala Thr His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
        115                 120                 125

Tyr Ser Lys Leu Asn Val Cys Ser Ile Ala Lys Arg Asn Pro Glu Ala
    130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Thr Asn Glu Pro Gln Lys Leu Lys Val
    210                 215                 220

Leu Leu Arg Asn Leu Arg Gly Glu Glu Asp Ser Pro Ser His Ile Lys
225                 230                 235                 240

Arg Thr Ser His Glu Ser Ala
                245
```